(12) United States Patent

Kleshinski et al.

(10) Patent No.: US 12,653,659 B2

(45) Date of Patent: Jun. 16, 2026

(54) METHODS AND SYSTEMS FOR PLACING EMBOLIC FILTERS IN AN AORTIC ARCH

(71) Applicant: Emboline, Inc., Santa Cruz, CA (US)

(72) Inventors: Stephen J. Kleshinski, Fremont, CA (US); Scott M. Russell, Santa Cruz, CA (US); Masao Drexel, Santa Cruz, CA (US); Amir Belson, Savyon (IL); Eric Storne, Menlo Park, CA (US); Matthew Davis, Auburn, CA (US)

(73) Assignee: Emboline, Inc., Santa Cruz, CA (US)

( * ) Notice: Subject to any disclaimer, the term of this patent is extended or adjusted under 35 U.S.C. 154(b) by 116 days.

(21) Appl. No.: 18/345,590

(22) Filed: Jun. 30, 2023

(65) Prior Publication Data

US 2023/0346536 A1 Nov. 2, 2023

Related U.S. Application Data

(63) Continuation-in-part of application No. PCT/US2021/060178, filed on Nov. 19, 2021.

(Continued)

(51) Int. Cl.
A61F 2/01 (2006.01)
A61F 2/24 (2006.01)

(52) U.S. Cl.
CPC .............. A61F 2/013 (2013.01); A61F 2/011 (2020.05); A61F 2/2433 (2013.01)

(58) Field of Classification Search
CPC .......... A61F 2/013; A61F 2/014; A61F 2/011; A61F 2/0105; A61F 2/2427
See application file for complete search history.

(56) References Cited

U.S. PATENT DOCUMENTS 4,723,549 A 2/1988 Wholey et al.
4,790,809 A 12/1988 Kuntz
(Continued)

FOREIGN PATENT DOCUMENTS

CA 2575865 A1 1/1998
CA 2609800 A1 1/2007
(Continued)

OTHER PUBLICATIONS

Russell et al.; U.S. Appl. No. 18/658,983 entitled "Integrated embolic protection devices," filed May 8, 2024.
(Continued)

*Primary Examiner* — Tuan V Nguyen
(74) *Attorney, Agent, or Firm* — Shay Glenn LLP

(57) ABSTRACT

An embolic filter positioning system includes a vascular delivery sheath, a filter catheter, a self-expanding embolic filter attached to a distal end of the filter catheter, and an elongate dilator having a tapered dilator tip. The elongate dilator is slidably received in a central lumen of the filter catheter, and the filter catheter is slidably received in the open lumen of the vascular delivery sheath. The tapered dilator tip is positioned distally of the distal end of the vascular delivery sheath, and the self-expanding embolic filter is radially constrained in a proximal portion of the open lumen of the vascular delivery sheath. The tapered dilator tip has an expanded configuration where it covers the open distal end of the vascular delivery sheath and facilitates entry though an arteriotomy and a contracted configuration where it can be retracted through the central lumen of the filter catheter.

20 Claims, 8 Drawing Sheets

Related U.S. Application Data

(60) Provisional application No. 63/151,508, filed on Feb. 19, 2021, provisional application No. 63/398,173, filed on Aug. 15, 2022.

(56) References Cited

U.S. PATENT DOCUMENTS

| | | | |
|---|---|---|---|
| 5,108,419 A | 4/1992 | Reger et al. |
| 5,197,485 A | 3/1993 | Grooters |
| 5,554,183 A | 9/1996 | Nazari |
| 5,643,227 A | 7/1997 | Stevens |
| 5,752,961 A | 5/1998 | Hill |
| 5,769,816 A | 6/1998 | Barbut et al. |
| 5,769,819 A | 6/1998 | Schwab et al. |
| 5,797,880 A | 8/1998 | Erskine |
| 5,800,525 A | 9/1998 | Bachinski et al. |
| 5,807,327 A | 9/1998 | Green et al. |
| 5,928,261 A | 7/1999 | Ruiz |
| 6,013,051 A | 1/2000 | Nelson |
| 6,083,239 A | 7/2000 | Addis |
| 6,117,154 A | 9/2000 | Barbut et al. |
| 6,120,534 A | 9/2000 | Ruiz |
| 6,129,739 A | 10/2000 | Khosravi |
| 6,139,517 A | 10/2000 | Macoviak et al. |
| 6,152,144 A | 11/2000 | Lesh et al. |
| 6,245,012 B1 | 6/2001 | Kleshinski |
| 6,254,563 B1 | 7/2001 | Macoviak et al. |
| 6,254,633 B1 | 7/2001 | Pinchuk et al. |
| 6,258,120 B1 | 7/2001 | McKenzie et al. |
| 6,348,063 B1 | 2/2002 | Yassour et al. |
| 6,355,051 B1 | 3/2002 | Sisskind et al. |
| 6,361,545 B1 | 3/2002 | Macoviak et al. |
| 6,371,935 B1 | 4/2002 | Macoviak et al. |
| 6,391,044 B1 | 5/2002 | Yadav et al. |
| 6,461,370 B1 | 10/2002 | Gray et al. |
| 6,499,487 B1 | 12/2002 | McKenzie et al. |
| 6,511,496 B1 | 1/2003 | Huter et al. |
| 6,537,297 B2 | 3/2003 | Tsugita et al. |
| 6,547,760 B1 | 4/2003 | Samson et al. |
| 6,682,543 B2 | 1/2004 | Barbut et al. |
| 6,692,513 B2 | 2/2004 | Streeter et al. |
| 6,695,864 B2 | 2/2004 | Macoviak et al. |
| 6,709,415 B2 | 3/2004 | Navia et al. |
| 6,712,834 B2 | 3/2004 | Yassour et al. |
| 6,746,469 B2 | 6/2004 | Mouw |
| 6,808,520 B1 | 10/2004 | Fourkas et al. |
| 7,044,958 B2 | 5/2006 | Douk et al. |
| 7,229,463 B2 | 6/2007 | Sutton et al. |
| 7,232,453 B2 | 6/2007 | Shimoln |
| 7,235,060 B2 | 6/2007 | Kraus |
| 7,537,600 B2 | 5/2009 | Eskuri |
| 7,758,606 B2 | 7/2010 | Streeter et al. |
| 7,766,932 B2 | 8/2010 | Melzer et al. |
| 7,959,662 B2 | 6/2011 | Erbel et al. |
| 8,052,717 B2 | 11/2011 | Mujkanovic et al. |
| 8,062,324 B2 | 11/2011 | Shimon et al. |
| 8,114,114 B2 | 2/2012 | Belson |
| 8,123,779 B2 | 2/2012 | Demond et al. |
| 8,298,258 B2 | 10/2012 | Anderson et al. |
| 8,308,754 B2 | 11/2012 | Belson |
| 8,337,519 B2 | 12/2012 | Wasick et al. |
| 8,382,788 B2 | 2/2013 | Gladonik et al. |
| 8,383,788 B2 | 2/2013 | Oliviero |
| 8,414,482 B2 | 4/2013 | Belson |
| 8,419,677 B2 | 4/2013 | Ducharme et al. |
| 8,420,902 B2 | 4/2013 | Gilsinger |
| 8,430,904 B2 | 4/2013 | Belson |
| 8,679,149 B2 | 3/2014 | Belson |
| 8,728,114 B2 | 5/2014 | Belson |
| 8,740,930 B2 | 6/2014 | Goodwin |
| 8,948,848 B2 | 2/2015 | Merhi |
| 8,968,354 B2 | 3/2015 | Wang et al. |
| 9,023,101 B2 | 5/2015 | Krahbichler |
| 9,107,734 B2 | 8/2015 | Belson |
| 9,144,485 B2 | 9/2015 | Bergheim |
| 9,427,252 B2 | 8/2016 | Sos |
| 9,492,265 B2 | 11/2016 | Russell et al. |
| 9,579,182 B2 | 2/2017 | Krahbichler |
| 9,668,849 B2 | 6/2017 | Ashkenazi |
| 9,744,023 B2 | 8/2017 | Wang et al. |
| 9,770,318 B2 | 9/2017 | Belson |
| 9,827,085 B2 | 11/2017 | Russell et al. |
| 9,844,387 B2 | 12/2017 | Merchand et al. |
| 9,877,821 B2 | 1/2018 | Russell et al. |
| 10,016,267 B2 | 7/2018 | Belson |
| 10,076,400 B2 | 9/2018 | Krahbichler |
| 10,130,331 B2 | 11/2018 | Stigall et al. |
| 10,166,094 B2 | 1/2019 | Russell et al. |
| 10,485,647 B2 | 11/2019 | Gera et al. |
| 10,500,033 B2 | 12/2019 | Naor et al. |
| 10,610,229 B2 | 4/2020 | Jonsson |
| 10,617,507 B2 | 4/2020 | Belson |
| 10,617,509 B2 | 4/2020 | Kleshinski et al. |
| 10,617,510 B2 | 4/2020 | Russell et al. |
| 10,675,139 B2 | 6/2020 | Von Mangoldtv et al. |
| 10,702,366 B2 | 7/2020 | Eli |
| 10,736,728 B2 | 8/2020 | Belson |
| 10,746,280 B2 | 8/2020 | Kamaguchi et al. |
| 10,870,340 B2 | 12/2020 | Acikgoez et al. |
| 10,881,494 B2 | 1/2021 | Belson |
| 10,939,987 B2 | 3/2021 | Belson |
| 11,000,357 B2 | 5/2021 | Ashkenazi et al. |
| 11,051,927 B2 | 7/2021 | Russell et al. |
| 11,071,844 B2 | 7/2021 | Merhi et al. |
| 11,246,698 B2 | 2/2022 | Zandi et al. |
| 11,304,792 B2 | 4/2022 | Russell et al. |
| 11,382,734 B2 | 7/2022 | Jone et al. |
| 11,399,927 B2 | 8/2022 | Kleshinski et al. |
| 11,623,068 B2 | 4/2023 | Sarabia |
| 11,707,351 B2 | 7/2023 | Jone et al. |
| 11,717,390 B2 | 8/2023 | Merhi et al. |
| 2001/0044632 A1 | 11/2001 | Daniel et al. |
| 2002/0004667 A1 | 1/2002 | Adams et al. |
| 2002/0045916 A1 | 4/2002 | Gray et al. |
| 2002/0058964 A1 | 5/2002 | Addis |
| 2002/0111648 A1 | 8/2002 | Kusleika et al. |
| 2002/0128680 A1 | 9/2002 | Addis |
| 2002/0143362 A1 | 10/2002 | Macoviak et al. |
| 2002/0161394 A1 | 10/2002 | Macoviak et al. |
| 2003/0040736 A1 | 2/2003 | Stevens |
| 2003/0040772 A1 | 2/2003 | Hoyodoh et al. |
| 2003/0100940 A1 | 5/2003 | Yodfat |
| 2003/0125765 A1 | 7/2003 | Blackledge et al. |
| 2003/0144686 A1 | 7/2003 | Martinez et al. |
| 2003/0176884 A1 | 9/2003 | Berrada et al. |
| 2003/0187474 A1 | 10/2003 | Keegan et al. |
| 2003/0208224 A1 | 11/2003 | Broome |
| 2004/0006364 A1 | 1/2004 | Ladd |
| 2004/0034380 A1 | 2/2004 | Woolfson et al. |
| 2004/0073253 A1 | 4/2004 | Morrill et al. |
| 2004/0138692 A1 | 7/2004 | Phung et al. |
| 2004/0225354 A1 | 11/2004 | Allen et al. |
| 2005/0060017 A1 | 3/2005 | Fischell et al. |
| 2005/0075724 A1 | 4/2005 | Svanidze et al. |
| 2005/0137688 A1 | 6/2005 | Salahieh et al. |
| 2005/0137696 A1 | 6/2005 | Salahieh et al. |
| 2005/0159773 A1 | 7/2005 | Broome et al. |
| 2005/0203569 A1 | 9/2005 | Kusleika et al. |
| 2005/0209609 A1 | 9/2005 | Wallace |
| 2005/0283186 A1 | 12/2005 | Berrada et al. |
| 2005/0283231 A1 | 12/2005 | Haug et al. |
| 2006/0100658 A1 | 5/2006 | Obana et al. |
| 2006/0129181 A1 | 6/2006 | Callol et al. |
| 2006/0135977 A1 | 6/2006 | Thompson et al. |
| 2006/0173490 A1 | 8/2006 | Lafontaine et al. |
| 2006/0287668 A1 | 12/2006 | Fawzi et al. |
| 2006/0293706 A1 | 12/2006 | Shimoin |
| 2007/0027534 A1 | 2/2007 | Bergheim et al. |
| 2007/0060944 A1 | 3/2007 | Boldenow et al. |
| 2007/0073246 A1 | 3/2007 | Simon |
| 2007/0073332 A1 | 3/2007 | Miller et al. |
| 2007/0118165 A1 | 5/2007 | DeMello et al. |
| 2007/0142858 A1 | 6/2007 | Bates |
| 2008/0027481 A1 | 1/2008 | Gilson et al. |

(56) References Cited

U.S. PATENT DOCUMENTS

| | | |
|---|---|---|
| 2008/0234722 A1 | 9/2008 | Bonnette et al. |
| 2008/0243081 A1* | 10/2008 | Nance .................... A61B 1/015 |
| | | 604/164.03 |
| 2008/0255603 A1 | 10/2008 | Naor et al. |
| 2009/0118760 A1 | 5/2009 | Clausen et al. |
| 2009/0149881 A1 | 6/2009 | Vale et al. |
| 2009/0254172 A1 | 10/2009 | Grewe |
| 2010/0010535 A1 | 1/2010 | Mujkanovic et al. |
| 2010/0106180 A1 | 4/2010 | Strother et al. |
| 2010/0191326 A1 | 7/2010 | Alkhatib |
| 2010/0262219 A1 | 10/2010 | Frimerman |
| 2010/0274277 A1 | 10/2010 | Eaton |
| 2010/0286768 A1 | 11/2010 | Alkhatib |
| 2010/0305604 A1 | 12/2010 | Pah |
| 2011/0137399 A1 | 6/2011 | Chomas et al. |
| 2012/0016408 A1 | 1/2012 | Barbut et al. |
| 2012/0078237 A1* | 3/2012 | Wang .................... A61F 2/2433 |
| | | 606/1 |
| 2012/0109056 A1* | 5/2012 | Rasmussen ....... A61M 25/0069 |
| | | 604/96.01 |
| 2012/0172915 A1 | 7/2012 | Fifer et al. |
| 2012/0172918 A1 | 7/2012 | Fifer et al. |
| 2012/0271340 A1 | 10/2012 | Castellano et al. |
| 2012/0271341 A1 | 10/2012 | Hill et al. |
| 2012/0289996 A1 | 11/2012 | Lee et al. |
| 2012/0330346 A1 | 12/2012 | Frimerman |
| 2012/0330348 A1 | 12/2012 | Strauss et al. |
| 2013/0046330 A1 | 2/2013 | McIntosh et al. |
| 2013/0096606 A1 | 4/2013 | Bruchman et al. |
| 2013/0158654 A1 | 6/2013 | Sutton et al. |
| 2013/0245669 A1 | 9/2013 | Basu et al. |
| 2013/0267993 A1 | 10/2013 | Carpenter |
| 2014/0000091 A1 | 1/2014 | Angel et al. |
| 2014/0005540 A1 | 1/2014 | Merhi |
| 2014/0058372 A1 | 2/2014 | Belson |
| 2014/0074152 A1 | 3/2014 | Shezifi et al. |
| 2014/0214069 A1 | 7/2014 | Franklin |
| 2014/0249568 A1 | 9/2014 | Adams et al. |
| 2014/0257362 A1 | 9/2014 | Eidenschink |
| 2014/0277087 A1 | 9/2014 | Manning |
| 2014/0277089 A1 | 9/2014 | Goode et al. |
| 2014/0277096 A1 | 9/2014 | Richter et al. |
| 2014/0343595 A1 | 11/2014 | Monstadt et al. |
| 2015/0006607 A1 | 1/2015 | E |
| 2015/0032120 A1 | 1/2015 | Janardhan et al. |
| 2015/0039016 A1 | 2/2015 | Naor et al. |
| 2015/0257868 A1 | 9/2015 | Shezifi |
| 2015/0320540 A1 | 11/2015 | Belson |
| 2015/0342717 A1 | 12/2015 | O'Donnell et al. |
| 2015/0366650 A1 | 12/2015 | Zi et al. |
| 2016/0106531 A1 | 4/2016 | Shezifi |
| 2016/0193045 A1 | 7/2016 | Pollak |
| 2016/0235515 A1 | 8/2016 | Merhi |
| 2016/0296315 A1 | 10/2016 | Yachia et al. |
| 2016/0317276 A1 | 11/2016 | Groh |
| 2016/0317277 A1 | 11/2016 | Carpenter et al. |
| 2016/0324621 A1 | 11/2016 | Shezifi et al. |
| 2016/0367285 A1 | 12/2016 | Sos |
| 2017/0143356 A1 | 5/2017 | Zandi et al. |
| 2017/0181835 A1* | 6/2017 | Kleshinski .............. A61F 2/013 |
| 2018/0008392 A1 | 1/2018 | Shemesh et al. |
| 2018/0206970 A1 | 7/2018 | Eggert et al. |
| 2019/0015152 A1 | 1/2019 | Howard et al. |
| 2019/0076231 A1 | 3/2019 | Ashkenazi |
| 2020/0054432 A1 | 2/2020 | Martin |
| 2020/0281717 A1 | 9/2020 | Spence |
| 2021/0045759 A1 | 2/2021 | Black et al. |
| 2021/0052375 A1 | 2/2021 | Jones et al. |
| 2021/0085445 A1 | 3/2021 | Ashkenazi et al. |
| 2021/0153999 A1 | 5/2021 | Eli et al. |
| 2021/0161638 A1 | 6/2021 | Belson |
| 2021/0220110 A1 | 7/2021 | Ashkenazi et al. |
| 2021/0315680 A1 | 10/2021 | Russell et al. |
| 2021/0322160 A1 | 10/2021 | Huber |
| 2022/0008186 A1 | 1/2022 | Belson |
| 2022/0168087 A1 | 6/2022 | Pasquino et al. |
| 2022/0265414 A1 | 8/2022 | Russell et al. |
| 2022/0331084 A1 | 10/2022 | Goslau et al. |
| 2022/0346932 A1 | 11/2022 | Zandi et al. |
| 2023/0070800 A1 | 3/2023 | Jones et al. |
| 2023/0091397 A1 | 3/2023 | Kleshinski et al. |
| 2023/0116973 A1 | 4/2023 | Yang et al. |
| 2023/0210650 A1 | 7/2023 | Kleshinski et al. |
| 2023/0293282 A1 | 9/2023 | Kleshinski et al. |
| 2024/0016596 A1 | 1/2024 | Martin |
| 2024/0245510 A1 | 7/2024 | Von Oepen et al. |
| 2024/0299151 A1 | 9/2024 | Montgomery |

FOREIGN PATENT DOCUMENTS

| | | | |
|---|---|---|---|
| CN | 1278713 A | 1/2001 |
| CN | 1331956 A | 1/2002 |
| CN | 101351242 | 1/2009 |
| CN | 201798779 U | 4/2011 |
| CN | 102186427 A | 9/2011 |
| CN | 102256566 A | 11/2011 |
| CN | 102811679 A | 12/2012 |
| CN | 102973332 A | 3/2013 |
| CN | 104434263 A | 3/2015 |
| CN | 105188604 A | 12/2015 |
| CN | 107072770 A | 8/2017 |
| CN | 108852555 A | 11/2018 |
| EP | 1179321 A2 | 2/2002 |
| EP | 3403615 A1 | 11/2018 |
| JP | H09276414 A | 10/1997 |
| JP | 2002542879 A | 12/2002 |
| JP | 2003508114 A | 3/2003 |
| JP | 2003526451 A | 9/2003 |
| JP | 2007527264 A | 9/2007 |
| JP | 2010517622 A | 5/2010 |
| JP | 4712707 B2 | 6/2011 |
| JP | 2015510788 A | 4/2015 |
| JP | 2016523119 A | 8/2016 |
| JP | 2017514563 A | 6/2017 |
| JP | 2018502690 A | 2/2018 |
| JP | 2018538027 A | 12/2018 |
| WO | WO96/01591 A1 | 1/1996 |
| WO | WO00/07656 A1 | 2/2000 |
| WO | WO00/27292 A1 | 5/2000 |
| WO | WO01/97714 A1 | 12/2001 |
| WO | WO03/043538 A2 | 5/2003 |
| WO | WO03/047648 A2 | 6/2003 |
| WO | WO03/073961 A1 | 9/2003 |
| WO | WO03/094791 A2 | 11/2003 |
| WO | WO2004/019817 A1 | 3/2004 |
| WO | WO2004/021922 A2 | 3/2004 |
| WO | WO2006/138391 A2 | 12/2006 |
| WO | WO2008/066881 A1 | 6/2008 |
| WO | WO2009/002548 A1 | 12/2008 |
| WO | WO2009/038799 A1 | 3/2009 |
| WO | WO2013/103979 A1 | 7/2013 |
| WO | WO2014/059005 A1 | 4/2014 |
| WO | WO2015/185870 A1 | 12/2015 |
| WO | WO2016/040923 A2 | 3/2016 |
| WO | WO2017/074530 A1 | 5/2017 |
| WO | WO2017/116828 A1 | 7/2017 |
| WO | WO2018/071508 A1 | 4/2018 |
| WO | WO2019/089821 A1 | 5/2019 |
| WO | WO2020/168091 A1 | 8/2020 |
| WO | WO2021/087480 A1 | 5/2021 |
| WO | WO2022/177618 A1 | 8/2022 |
| WO | WO2023/205022 A1 | 10/2023 |

OTHER PUBLICATIONS

Belson et al.; U.S. Appl. No. 18/857,805 entitled "Embolic protection for mitral and tricuspid valve procedures," filed Oct. 17, 2024.
Russell et al.; U.S. Appl. No. 19/037,061 entitled "Catheter with integrated embolic protection device," filed Jan. 24, 2025.

* cited by examiner

METHODS AND SYSTEMS FOR PLACING EMBOLIC FILTERS IN AN AORTIC ARCH

CROSS-REFERENCE TO RELATED APPLICATIONS

This application is a continuation-in-part of PCT Application No. PCT/US2021/60178, filed Nov. 19, 2021, which claims the benefit of provisional patent application Ser. No. 63/151,508, filed on Feb. 19, 2021, the full disclosures of which are incorporated herein by reference; this application also claims the benefit of U.S. Provisional No. 63/398,173, filed Aug. 15, 2022, the entire content of which is incorporated herein by reference.

BACKGROUND OF THE INVENTION

1. Field of the Invention

The present invention relates generally to medical apparatus and methods and more particularly to methods and systems for placing embolic filters in a patient's aortic arch prior to transcatheter aortic valve replacement (TAVR) and other aortic valve procedures.

Transcatheter aortic valve replacement (TAVR) has become a preferred alternative to open heart surgery for many patients needing aortic valve replacement. The most common approach is "transfemoral" where the femoral artery is accessed via a small incision in the groin, and the replacement valve is advanced from the femoral artery into the descending aorta and over the aortic arch using a specialized delivery catheter.

While highly successful, transfemoral and other TAVR procedures can release emboli and present a significant risk of cerebral embolism. Embolic particles, such as thrombus, atheroma and lipids, may become dislodged by advancement and manipulation of the delivery catheter and enter the bloodstream, embolizing in the brain or other vital organs downstream. Cerebral embolism can lead to neuropsychological deficits, stroke and even death. Other organs downstream can also be damaged by embolism, resulting in diminished function or organ failure.

For these reasons, the use of an embolic protection system during TAVR and other catheter-based procedures has been proposed. For example, commonly owned U.S. Pat. No. 10,617,509, describes a cylindrical embolic filter and a system for placing the filter into a patient's aortic arch for reducing the risk of cerebral aneurysm and other negative outcomes caused by the release of emboli during TAVR. The embolic filter is placed by introducing a convention dilator and access sheath assembly 10, as shown in FIG. 1, though the femoral artery. The sheath assembly 10 comprises a tubular access sheath 12 and a dilator 14 having a tapered distal tip 16. The dilator tip 16 is solid, and the dilator 14 has a guidewire lumen (not shown) extending axially therethrough to receive a guidewire 18. As the dilator 14 and tip 16 are solid and one piece, the entire dilator must be removed from the access sheath 12 to free the access sheath lumen to introduce a filter delivery catheter. As described in U.S. Pat. No. 10,617,509, the separate filter delivery catheter is introduced into the access sheath lumen using a peel-away sheath after removing the dilator. While fully workable, the time needed to remove the dilator, place the peel-away sheath, and introduce the filter delivery catheter is significant and adds to the overall procedure time.

For those reasons, it would be advantageous to provide improved methods and systems for introducing embolic filters into a patient's aortic arch for embolic protection during TAVR and other cardiac and vascular procedures. In particular, it would be advantageous to reduce the number of steps need to deploy such embolic filters and/or to reduce an overall procedure time. At least some of these objectives will be met by the inventions described and claimed herein.

2. Description of the Background Art

U.S. Pat. No. 10,617,509, has been described above. WO2017/116828 and US2020/0197151 are related to U.S. Pat. No. 10,617,509. Other devices for inhibiting cerebral embolism are described in the following commonly patents and patent applications, which are hereby incorporated by reference: U.S. Pat. No. 10,166,094, for Catheter with integrated embolic protection device; U.S. Pat. No. 9,877,821 for Introducer sheath with embolic protection; U.S. Pat. No. 6,254,563 for Perfusion shunt apparatus and method; U.S. Pat. App. 2010/0312268 for Embolic protection device; U.S. Pat. App. 2004/0215167 for Embolic protection device; PCT App. WO2004/019817 for Embolic protection device; U.S. Pat. No. 6,371,935 for Aortic catheter with flow divider and methods for preventing cerebral embolization; U.S. Pat. No. 6,361,545 for Perfusion filter catheter; U.S. Pat. No. 6,254,563 for Perfusion shunt apparatus and method; U.S. Pat. No. 6,139,517 for Perfusion shunt apparatus and method; U.S. Pat. No. 6,537,297 for Methods of protecting a patient from embolization during surgery; U.S. Pat. No. 6,499,487 for Implantable cerebral protection device and methods of use; U.S. Pat. No. 5,769,816 for Cannula with associated filter; and U.S. Pat. App. 2003/0100940 for Implantable intraluminal protector device and method of using same for stabilizing atheroma. See also U.S. Pat. No. 8,419,677 and US2012/0109056.

SUMMARY OF THE INVENTION

In a first aspect, the present invention provides a method for positioning an embolic filter in a patient's aortic arch The method comprises providing an embolic filter positioning assembly including a dilator component that facilitates introduction into the patient's vasculature ands reduces the steps and time need to place the embolic filter in the aortic arch. The embolic filter positioning assembly includes (1) a vascular delivery sheath, (2) a filter catheter slidably received in an open lumen of said vascular delivery sheath, (3) an elongate dilator having a guidewire lumen slidably received in a central lumen of the filter catheter, (4) a tapered dilator tip attached at a distal end of the elongate dilator, and (5) an embolic filter carried on a distal portion of the filter catheter. The tapered dilator tip is expanded and positioned to extend distally beyond and cover an open distal end of the vascular delivery sheath, and the expanded tapered dilator tip of the embolic filter positioning assembly is introduced though an arteriotomy, over a first guidewire received in the guidewire lumen of the elongate dilator, and into the patient's arterial vasculature. A distal end of the embolic filter positioning assembly is advanced to position the embolic filter carried on the distal portion of the filter catheter in the patient's aortic arch, and a distal potion of the vascular delivery sheath is retracted from over the embolic filter, and the embolic filter is expanded within the patient's aortic arch. The tapered dilator tip may then be contracted, and the tip retracted proximally into or through the central lumen of the filter catheter.

In some examples of these methods, expanding the tapered dilator tip may comprise inflating the tapered dilator tip and contracting the tapered dilator tip comprises deflating the tapered dilator tip. In other examples, the tapered dilator tip may be configured for mechanical expansion, for example, comprising a mechanically expandable wire or other frame (e.g., expanded by retracting a pull wire to axially foreshorten the frame to cause radial expansion) covered by a membrane, typically a fluid impermeable membrane.

In some examples of these methods, the tapered dilator tip may have a conical geometry with a base and positioning the tapered dilator tip to extend distally beyond and cover an open distal end of the vascular delivery sheath comprises detachably mating the base with the open distal end of the vascular delivery sheath. In some instances, the base of the tapered dilator tip may be cylindrical and configured to fit inside the open distal end of the vascular delivery sheath.

In some examples of these methods, a proximal end of the embolic filter may be closed and the filter may be retracted back into the vascular delivery sheath. In specific instances, closing the proximal end of the embolic filter may comprises ratcheting a lasso on the proximal end of the embolic filter.

In some examples of these methods, the embolic filter self-expands within the patient's aortic arch after the distal portion of the vascular sheath is retracted from over the embolic filter.

In a second aspect, the present invention provides method for implanting a prosthetic aortic valve in a patient's aortic arch. The method comprises placing an embolic filter in the patient's aortic arch by any of the methods described above and elsewhere herein. The prosthetic aortic valve is advanced through the embolic filter, and the prosthetic aortic valve is deployed in the patient's aortic annulus while the embolic filter remains in place in the aortic arch.

In some examples of such valve implantation methods, advancing the prosthetic aortic valve through the embolic filter comprises removing the elongate dilator from the central lumen of the filter catheter leaving the first guidewire in place in the central lumen of the filter catheter. The first guidewire is then exchanged for an angiography pigtail catheter, and one or more valve placement guidewires are advanced through the embolic filter and over the aortic arch in parallel to the embolic filter positioning assembly. A valve placement catheter carrying the prosthetic valve is then advanced over the one or more valve placement guidewires to the aortic annulus or other target location.

In a third aspect, the present invention provides an embolic filter positioning system which comprises (1) a vascular delivery sheath having a proximal hemostasis valve, an open distal end, and an open lumen extending from the open distal end to the hemostasis valve, (2) a filter catheter having a proximal end, a distal end, and a central lumen therethrough, (3) a self-expanding embolic filter attached to the distal end of the filter catheter, (4) an elongate dilator having a proximal end, a distal end, and a guidewire lumen therethrough, and (5) a tapered dilator tip attached at the distal end of the elongate dilator. The elongate dilator is configured to be slidably received in the central lumen of the filter catheter, and the filter catheter is configured to be slidably received in the open lumen of the vascular delivery sheath. The tapered dilator tip is positionable distally of the distal end of the vascular delivery sheath, and the self-expanding embolic filter is configured to be radially constrained in a proximal portion of the open lumen of the vascular delivery sheath. The tapered dilator tip has an expanded configuration where it covers the open distal end of the vascular delivery sheath and facilitates entry though an arteriotomy and a contracted configuration where it can be retracted through the central lumen of the filter catheter.

In some examples of the embolic filter positioning systems of the present invention, the tapered dilator tip may have a conical geometry with a base configured to detachably mate with the open distal end of the vascular delivery sheath. In particular instances, the base of the tapered dilator tip may be cylindrical and configured to fit inside the open distal end of the vascular delivery sheath.

In other examples, the embolic filter positioning systems of the present invention may further comprise a handle attached to the proximal end of the filter catheter. In particular instances, the handle may comprise a mechanism for closing a proximal end of the embolic filter prior to retraction of the filter back into the vascular delivery sheath, for example the mechanism for closing a proximal end of the embolic filter may comprise a ratcheting retractor coupled to a lasso on the proximal end of the embolic filter.

In some examples of the embolic filter positioning systems of the present invention, the embolic filter may comprise a cylindrical body configured to self-expand in and conform to the inner wall of the patient's aortic arch. In particular instances, the embolic filter may further comprise a port extending across a central passage of cylindrical body, wherein the port is expandable and configured to seal against the outer surfaces of catheters and guidewires advanced therethrough. In other instances, the cylindrical body of the embolic filter may comprise comprises a porous material comprising a fabric of knitted, woven, or nonwoven fibers, filaments, or wires. For example, the porous material is made of a resilient metal, polymer material, a malleable material, a plastically deformable material, a shape-memory material, or combinations thereof. In other examples, the porous material may have a pore size chosen to prevent emboli over a predetermined size from passing through.

In a fourth aspect, the present invention provides a dilator sheath system comprising a vascular delivery sheath having a proximal hemostasis valve, an open distal end, and an open lumen extending from the open distal end to the hemostasis valve. The system further incudes an elongate dilator having a proximal end, a distal end, and a guidewire lumen therethrough. A tapered dilator tip is attached at the distal end of the elongate dilator, and the elongate dilator is configured to be slidably received in the central lumen of the vascular delivery sheath with the tapered dilator tip is positionable distally of the distal end of the vascular delivery sheath. The tapered dilator tip has an expanded configuration where it covers the open distal end of the vascular delivery sheath and facilitates entry though an arteriotomy and a contracted configuration where it can be retracted through the central lumen of the vascular delivery sheath, typically being an inflatable conical structure with an apical tip projecting distally from the vascular delivery sheath. In this way, the size of the access sheath can be minimized, and removal of the dilator can be simplified.

The tapered dilator tip typically has a conical geometry with a base configured to detachably mate with the open distal end of the vascular delivery sheath, usually having a base of the which is cylindrical and configured to fit inside the open distal end of the vascular delivery sheath.

In some examples, the dilator sheath system further comprises a hub attached to the proximal end of the vascular delivery sheath. The hub may further include a side port for introducing contrast or other purposes.

In a fifth aspect, the present invention provides a method of positioning a vascular delivery sheath in a patient's blood vessel. The method comprises providing a vascular delivery system including (1) the vascular delivery sheath and (2) an elongate dilator having a tapered dilator tip attached at a distal end thereof and a guidewire lumen, said elongate dilator being slidably received in a central lumen of the vascular delivery sheath. The tapered dilator tip is expanded and positioned to extend distally beyond and cover an open distal end of the vascular delivery sheath. The expanded tapered dilator tip of at the distal end of the vascular delivery is introduced though an arteriotomy, over a first guidewire received in the guidewire lumen of the elongate dilator, and into the patient's vasculature. The tapered dilator tip is contracted and retracted proximally into or through the central lumen of the filter catheter.

Typically, expanding the tapered dilator tip comprises inflating the tapered dilator tip and contracting the tapered dilator tip comprises deflating the tapered dilator tip.

Typically, the tapered dilator tip has a conical geometry with a base, and the tapered dilator tip is positioned to extend distally beyond and cover an open distal end of the vascular delivery sheath comprises detachably mating the base with the open distal end of the vascular delivery sheath. Foe example, the base of the tapered dilator tip may be cylindrical and configured to fit inside the open distal end of the vascular delivery sheath.

The methods of the present invention may further comprise delivering a vascular implant through the central lumen of the vascular delivery sheath, where the implant may be selected from a group consisting of a filter, a stent, a prosthetic valve, and a valve clip.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
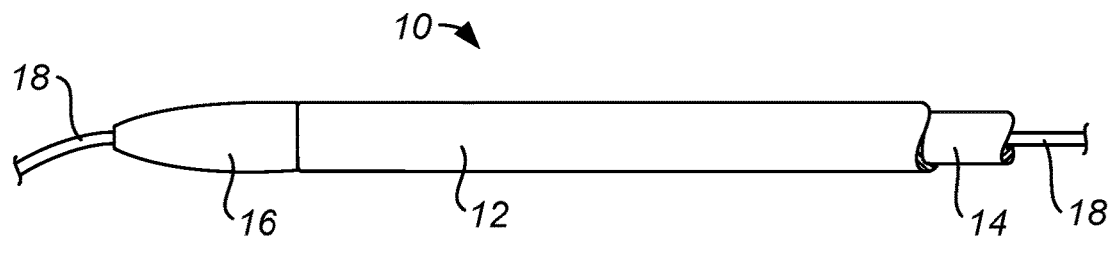
FIG. 1 shows a prior art endovascular sheath having a conventional solid dilator with a guidewire extending distally from a lumen of the dilator.

For purposes of this patent application, the term "distal" refers to the end of the device that is farthest away from the operator, and closest to the heart. This is also the "upstream" direction of blood flow. The term "proximal" refers to the end of the device nearer to the operator, toward the direction of the access site where the device has been introduced into the body, and farthest away from the heart. This is also the "downstream" direction of blood flow.

In the present invention, a conventional dilator is replaced with an "expandable tip catheter," typically a "balloon dilator," having a distal taper of similar profile to the tapered tip of a conventional dilator, attached to a smaller diameter shaft having a guidewire lumen to accommodate a guidewire with additional lumen(s) to enable inflation and deflation of the balloon. The construction may similar to a non-distensible balloon catheter used for angioplasty, where the shape of the balloon optimized to facilitate its use as a dilator, typically being a tapered cone with the narrow end facing in a distal direction. Suitable inflation media include liquids, such as saline, and gases, such as carbon dioxide.

A principal benefit of the balloon or other expandable dilator of the present invention is that the associated interventional or diagnostic catheter can be placed through a sheath and over the shaft of the balloon dilator (that is in turn over a guidewire), without the need for removal of the balloon dilator. In preferred embodiments, the interventional or diagnostic device can be preloaded over the balloon dilator in the sheath to save procedural time and enhance the ease of use of devices, which no longer require an initially introducing step through the proximal end of the sheath.

By way of example, an embolic protection filter may be made from a self-expanding material (e.g., a shape memory alloy) can be compressed and preloaded into the distal end of the sheath over the shaft of a balloon dilator. The balloon dilator can then be withdrawn until the balloon itself is located at the distal end of the sheath. The balloon can then be inflated to create a somewhat rigid distal taper that mates with the end of the sheath. This whole system can then be introduced over a guidewire, through a Seldinger puncture and advanced to the treatment location. The sheath is then withdrawn from around the filter, allowing the filter to expand into position. After filter deployment, the balloon is deflated and the entire balloon dilator system is withdrawn through the filter and attachment catheter lumen and removed, leaving the sheath, filter and guidewire behind.

The tapered balloon of the present invention could also be replaced with a mechanically expandable frame with a polymer covering, or any other expandable and contractable system that acts as a temporary dilator tip during insertion of the sheath through the Seldinger puncture.

Some delivery systems use a nose cone, or olive at the distal end replacing the traditional dilator and allowing for devices to be loaded over a smaller shaft at the distal end. In these cases, the olive can be either closely mated to the ID of the sheath, in which case, it is possible to remove it through the sheath, or matched to the OD of the sheath which prohibits its removal from the sheath. In the balloon dilator of the present invention, the diameter of the inflated balloon can be matched to the diameter of the sheath and still be removed because the balloon is collapsible, providing more flexibility for delivery or passage of other interventional devices.

In addition, as interventional procedures and devices increase in complexity, multi-catheter systems may be required for their delivery into the body. One example is a system comprised of four catheters in which each catheter has a separate function, while being able to be introduced through a singular arteriotomy. The first (outermost) catheter acts as a vehicle for access and removal within the vasculature of two additional devices. A second catheter is attached to, or carries, either a therapeutic, or a prophylactic device. A third balloon dilator catheter passes through the second catheter to allow for insertion through the arteriotomy. Finally, a diagnostic catheter replaces the balloon dilator catheter leaving three catheters with separate functions in a single arteriotomy. Any fixed diameter dilator, nose cone, or olive (as opposed to the collapsible balloon dilator) matched to the diameter of the outer catheter for use in crossing the arteriotomy, would therefore be too large to be removed through the second catheter, and therefore would require a second puncture/access site for placement of the diagnostic catheter.

Figure 2A:
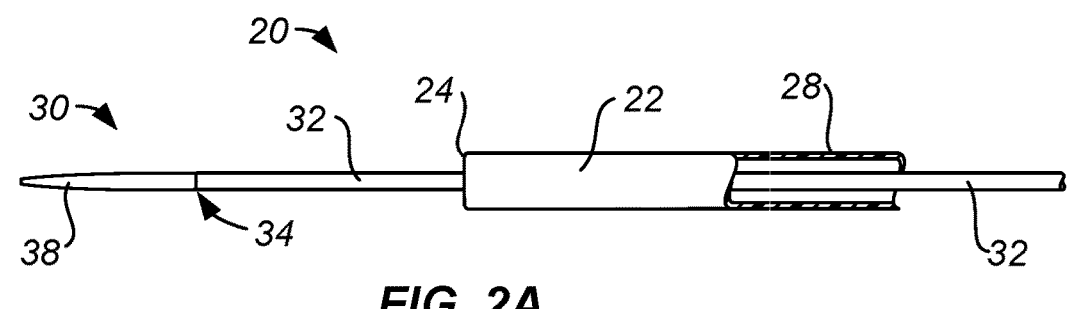
FIGS. 2A-2C show a distal portion of a vascular delivery sheath according to the present invention with the balloon dilator uninflated in FIG. 2A, the balloon dilator inflated in FIG. 2B, and the inflated balloon dilator drawn proximally into the distal tip of the sheath in FIG. 2C.
Figure 2B:
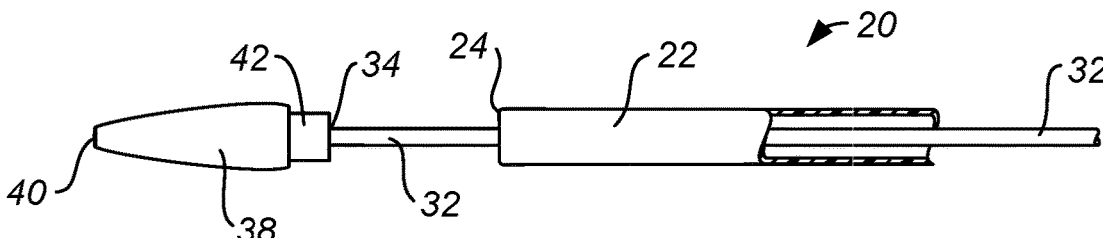
Figure 2C:
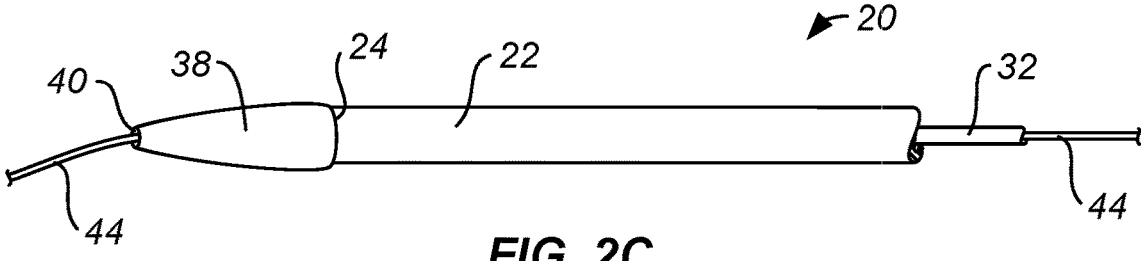

Referring now to FIGS. 2A-2C, 3, and 4, a vascular delivery sheath assembly 20 according to the present invention comprises a vascular delivery sheath 22 having an open distal end 24, a proximal end 26 (FIG. 3), and a lumen 28 therethrough. A dilator 30 comprises a shaft 32 having a distal end 34, a proximal end (not shown), and an inflatable tip 38 at its distal end. The inflatable tip 38 is shown in its uninflated condition in FIG. 2A. The tip 38 is shaped to be inflated into a tapered profile, typically a conical profile, as shown in FIG. 2B. The conical configuration includes a narrow or pointed distal end 40 and a cylindrical base 42 at its proximal end. As shown in FIG. 2C, the dilator shaft 32 may be pulled proximally in order to draw the base 42 into the distal opening 24 of the vascular delivery sheath 22. Once the inflated distal tip 38 is fully proximally retracted, as shown in FIG. 2C, the vascular delivery sheath assembly 20 is ready to be introduced over a guidewire 44 and used in the vascular procedures of the present invention as described more fully below. The sheath 22 typically includes a hemostatic valve 46 which may include a side port 48 for introducing contrast or other purposes. The dilator 30 has a guidewire lumen (not shown) and typically includes a hub 50 with a hemostatic port 52 for receiving the guidewire 44 and an inflation port 54 for inflating the inflatable tip 38.

Figures 3, 4, 5:
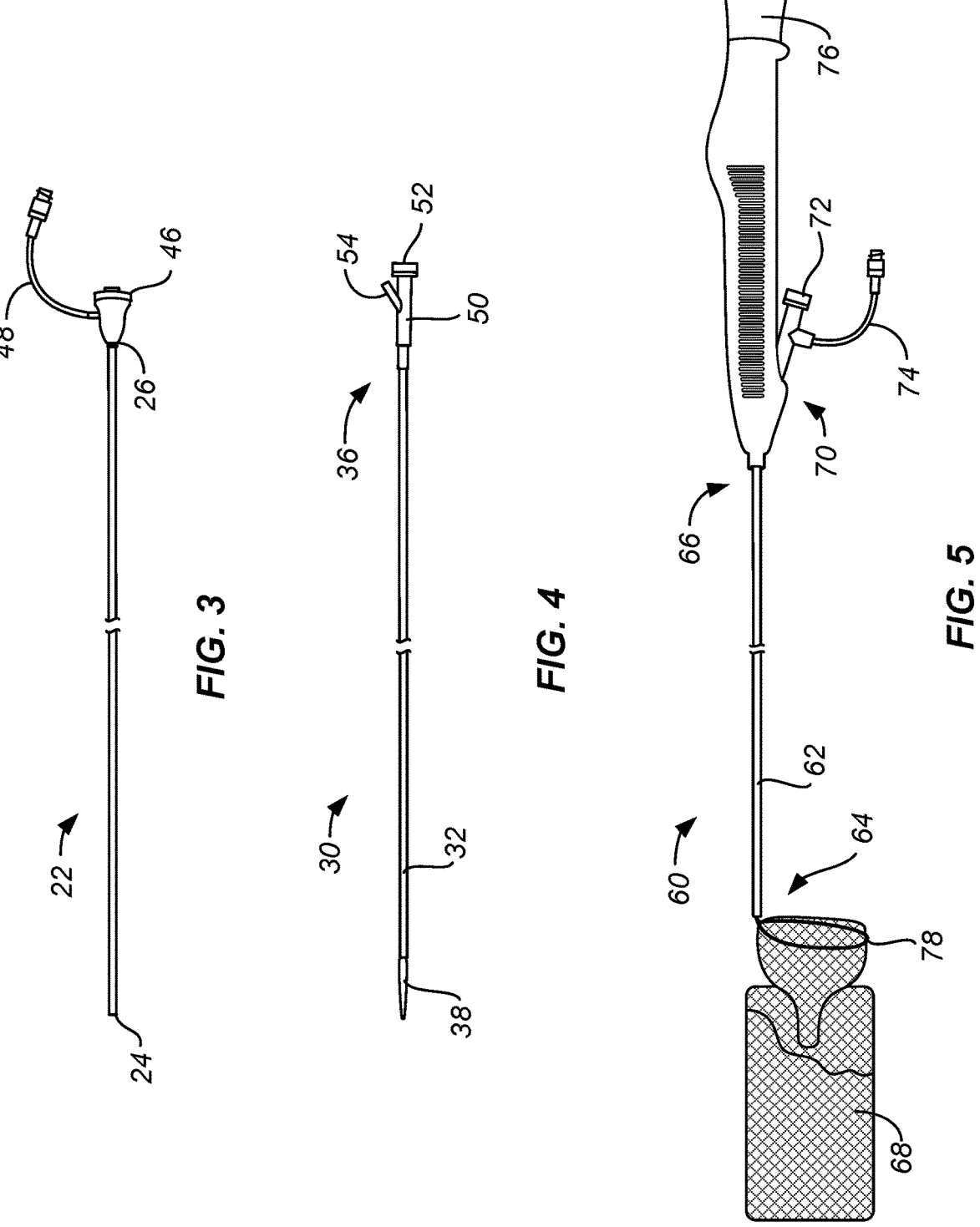
FIG. 3 shows the full-length sheath of FIGS. 2A-2C including a hemostatic valve at its proximal end and without the dilator.
FIG. 4 shows the full-length dilator of the vascular delivery sheath of FIGS. 2A-2C including a proximal hub.
FIG. 5 shows a filter catheter according to the present invention having an embolic filter at its distal end and a handle at its proximal end.

Referring now to FIG. 5, a filter catheter 60 comprises a shaft 62 having a distal end 64 and a proximal end 66. The shaft 62 will be dimensioned to fit within the lumen of the vascular delivery sheath 22, as will be described in more detail below. The shaft 62 will typically itself include a lumen or central passage for connecting a purse string loop

8

Figures 10A, 10B:
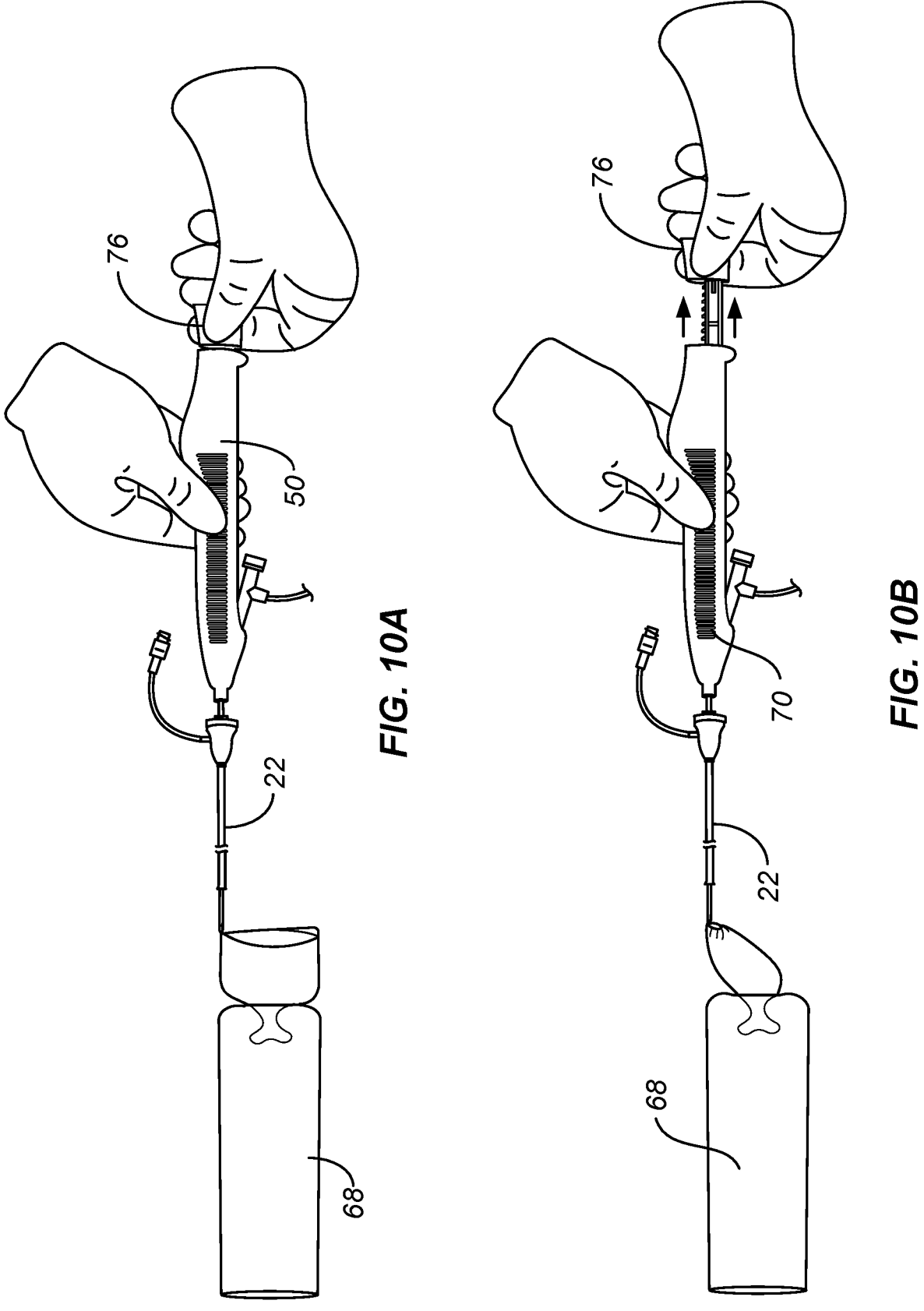
FIGS. 10A and 10B illustrate use of a ratcheting mechanism for closing an end of the embolic filter prior to drawing the filter back into the delivery sheath.

78 at the distal end 64 to a handle 70 at the proximal end 66. An embolic filter 68, typically a self-expanding cylindrical mesh filter of the type described in commonly owned US Patent Publication No. 2020/0253709, the full disclosure of which is incorporated herein by reference, is secured to the distal end 64 of the shaft 62, typically by the purse string loop 78. The handle 70 includes a side port 72, typically configured to receive the dilator 30 and/or associated guidewires, and a ratchet pull 76. The ratchet pull is configured to be "ratcheted," as shown in FIGS. 10A and 10B, to apply a proximal tension on the purse string 78 in order to close a proximal end of the embolic filter, as shown in FIG. 10B.

Figure 6:
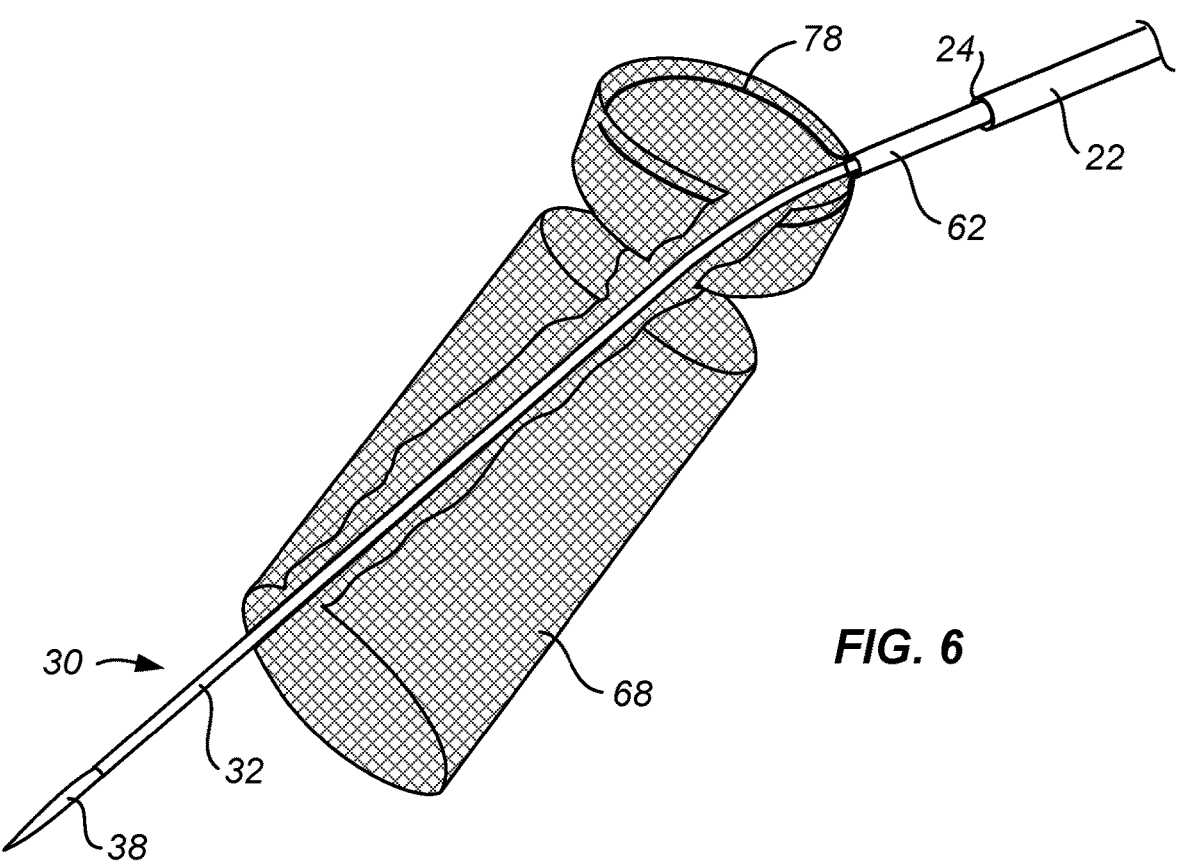
FIG. 6 is a detailed view with portions broken away showing the embolic filter attached at a distal end of a filter catheter shaft and having the vascular delivery sheath assembly positioned therethrough with an inflatable tip in its deflated configuration.

Referring now to FIG. 6, to prepare the vascular delivery sheath assembly 20 for introduction to a patient, the dilator 30 is first introduced through the lumen of shaft 62 so that it extends through the interior of the embolic filter 68. A subassembly of the dilator 30 and the filter catheter 60 is then advanced into the vascular delivery sheath 22 so that they together extend beyond the distal open and 24 of sheath 22.

Figure 7:
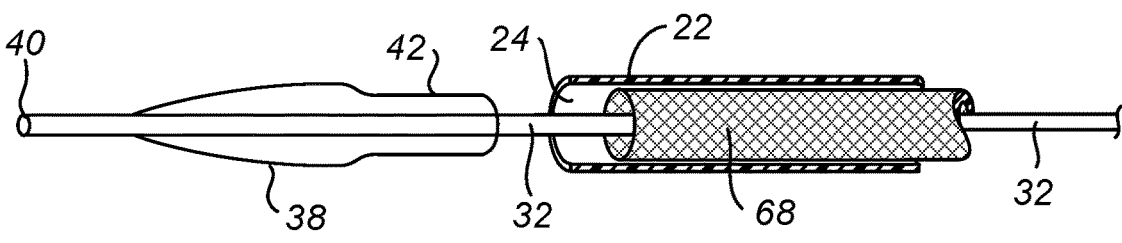
FIG. 7 is a detailed view knowing the inflatable tip of the dilator of the vascular delivery sheath assembly in its inflated configuration extending from the distal end of the vascular delivery sheath.
Figure 8:
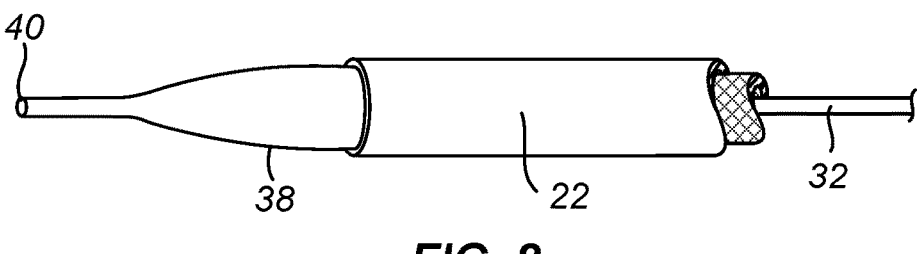
FIG. 8 is a detailed view similar to that of FIG. 7 where the inflated tip of the dilator has been drawn proximally into an open end of the vascular delivery sheath to a patient's femoral artery.

Referring now to FIGS. 7 and 8, the vascular delivery sheath assembly 24 is further prepared by retracting the embolic filter 68 through open end 24 of the sheath 22 so that it elongates and is radially constrained. The inflatable tip 38 of the dilator 30 is then inflated to assume its tapered configuration. The inflatable tip 38 is typically formed from a non-distensible material such as polyethylene terephthalate (PET), a nylon, or other material of a type used in fabricating angioplasty balloons. The inflatable tip will be inflated with a non-compressible fluid, typically saline, to a pressure sufficient to form a rigid body suitable for advancement into the femoral artery and through the patient's vasculature. In this way, during use, the inflatable tip will perform in a manner similar to a conventional solid-tip dilator.

After the inflatable tip 38 has been inflated, it can be retracted into the open end 24 of the vascular delivery sheath 22. When inflated, the inflatable tip 38 will typically have a generally conical shape with a pointed tip 40 and a cylindrical base 42, where the cylindrical base is sized and configured to mate with the open and 24 of the sheath and the dilator is retracted proximally within the sheath, as shown in FIG. 8.

Figure 9A:
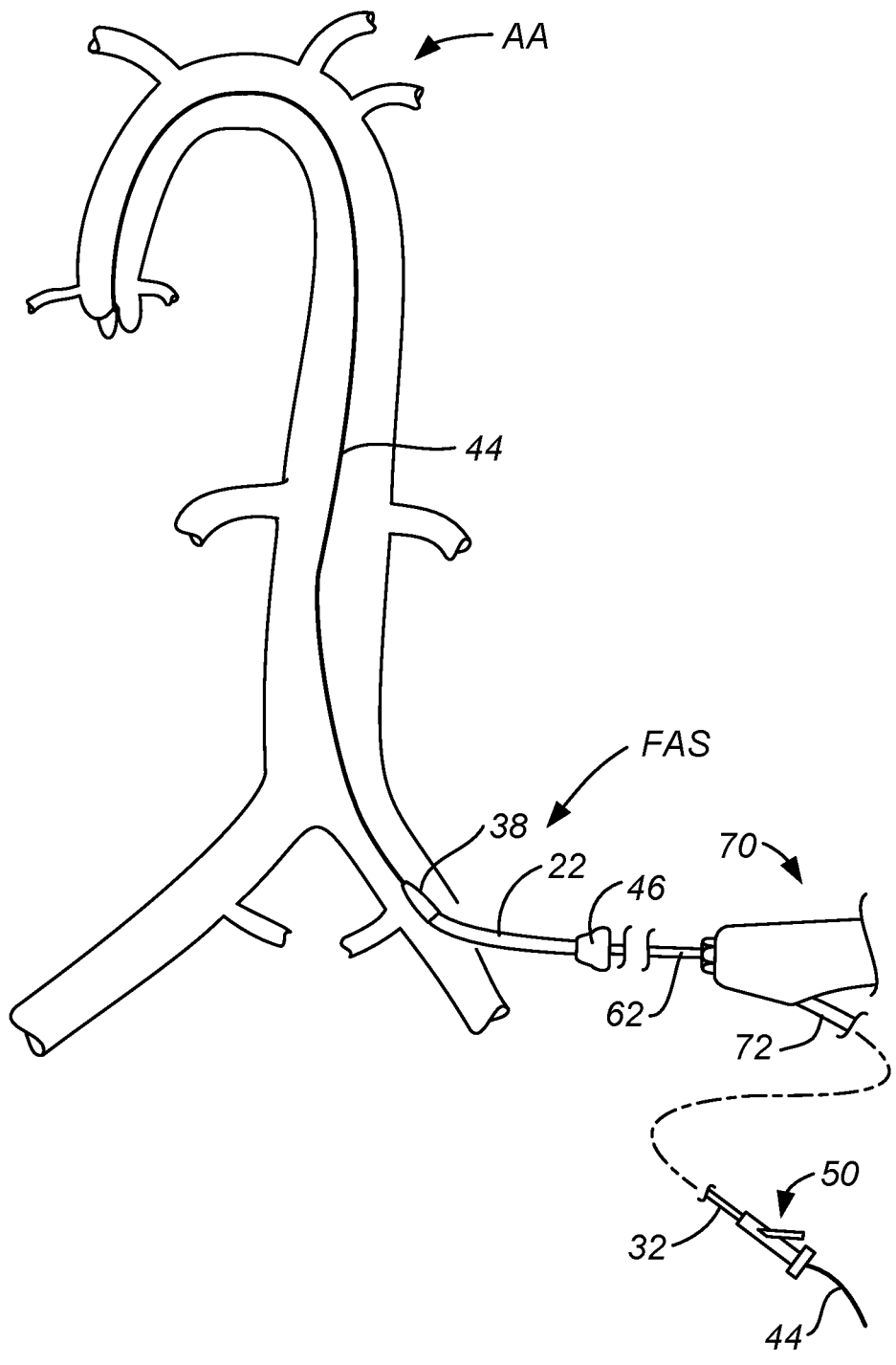
FIGS. 9A-9F illustrate use of the vascular delivery sheath assembly of the present invention for placing an embolic filter in a patient's aortic arch and thereafter implanting a prosthetic valve in the patient's aortic valve annulus.
Figure 9B:
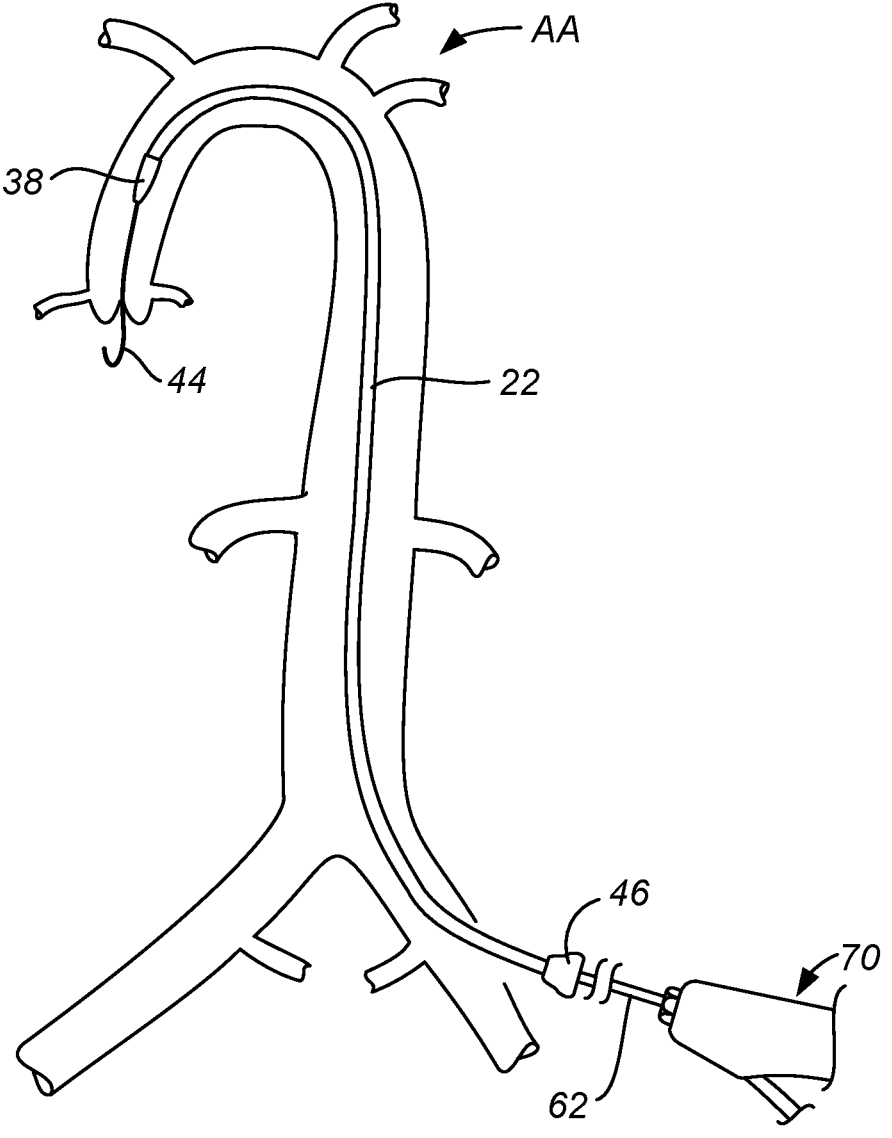

Referring now to FIGS. 9A-9F, use of the vascular delivery sheath assembly 20 for placing the embolic filter 68 in a patient's aortic arch AA will be described. With the distal region of the vascular delivery sheath assembly 20 in the configuration shown in FIGS. 2C and 8, the inflatable tip 38 is introduced over guidewire 44 through a femoral access site FAS. The inflated tip 38 acts in a manner identical to a conventional solid dilator at this stage of the intervention. The inflated tip 38 and vascular delivery sheath 22 are then advanced over the patient's aortic arch AA, as shown in FIG. 9B.

Figure 9C:
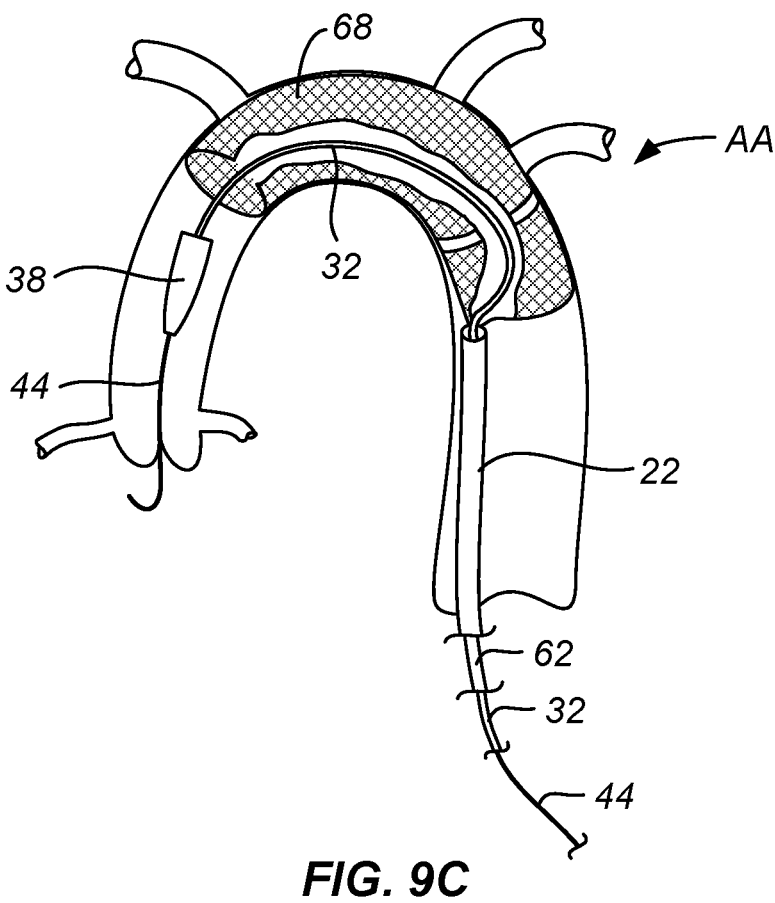
Figure 9D:
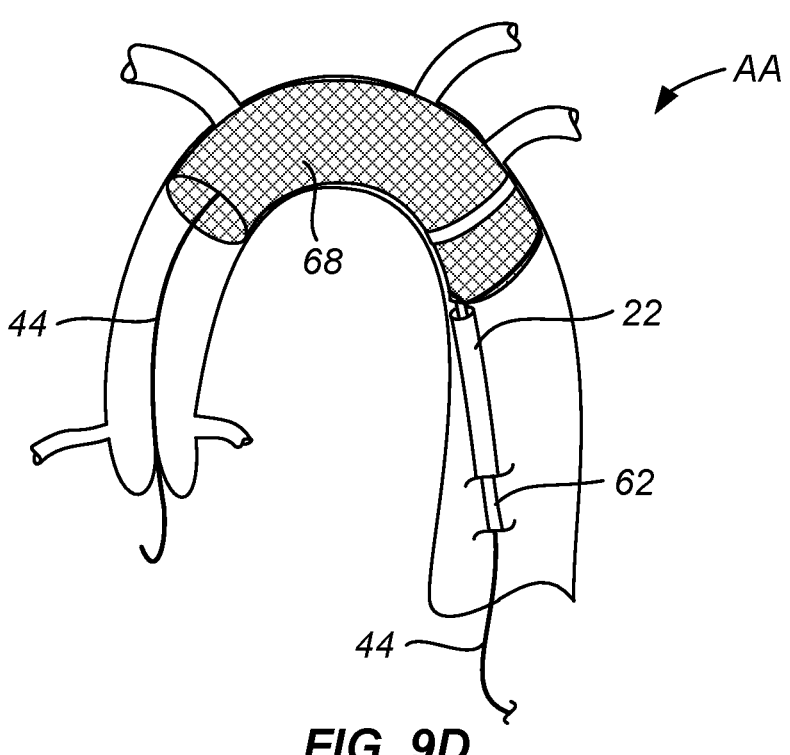

After the distal portion of the vascular delivery sheath assembly 20 reaches a target location over the aortic arch AA, the delivery sheath 22 will be retracted to deploy the embolic filter 68, as shown in FIG. 9C. Reflection may be achieved by pulling proximally on the hemostatic valve 46 at the proximal end of the sheath 22 to pull the sheath back over shaft 62 of the filter catheter 60, allowing the filter to self-expand. After the embolic filter has been employed, the inflatable tip 38 may be deflated and drawn proximally back into the lumen 28 of sheath 22. Typically, the entire dilator 30 will be removed from the sheath 22 at this point.

Figure 9E:
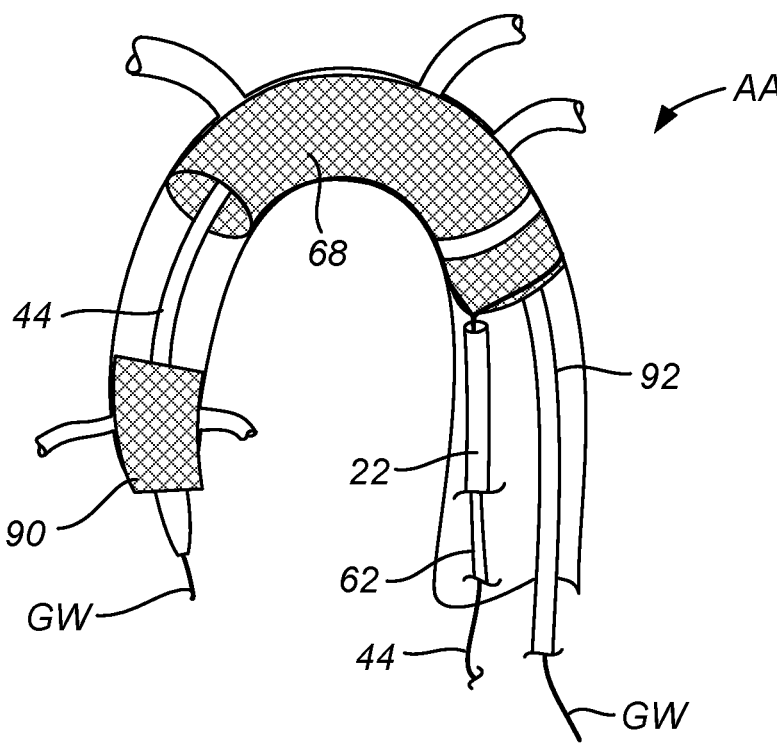

With the embolic filter 68 probably deployed, a separate guidewire GW can be introduced over the aortic arch AA and through the filter, and a delivery catheter 92 advanced over the guidewire GW, as shown in FIG. 9E. The delivery catheter 92 may be used to deliver any conventional prosthetic aortic valve, typically a balloon-expandable aortic valve, such as an Edwards Sapien® valve or a Medtronic CoreValve® heart. Details of how the valve can be introduced through embolic filter 68 are provided in commonly owned US Patent Publication No. 2020/0253709, the full disclosure which has been previously incorporated herein by reference.

Figure 9F:
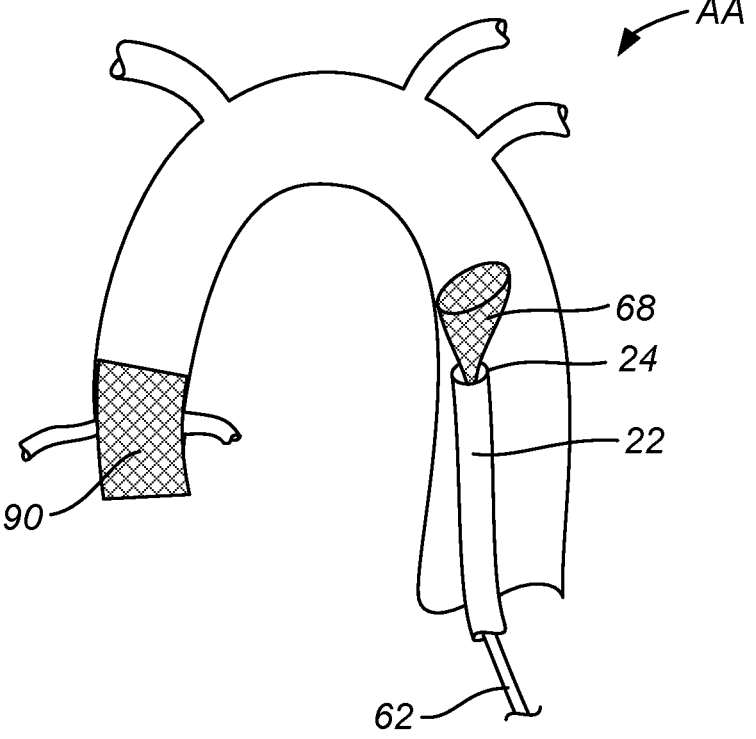

After the prosthetic aortic valve 90 has been properly implanted, the valve delivery catheter 90 can be removed followed by removal of the embolic filter 68, as shown in FIG. 9F. Typically, the ratchet pull 76 on the filter catheter handle 70 is used to drawdown the purse string loop 78 on the filter prior to drawing proximally on the filter catheter to pull the filter 68 into the open and 24 of the sheath 22, as shown in FIGS. 10A and 10B.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of positioning an embolic filter in a patient's aortic arch, said method comprising:

providing an embolic filter positioning assembly including (1) a vascular delivery sheath, (2) a filter catheter slidably received in an open lumen of said vascular delivery sheath, (3) an elongate dilator having a guidewire lumen slidably received in a central lumen of the filter catheter, (4) a tapered dilator tip attached at a distal end of the elongate dilator, and (5) an embolic filter carried on a distal portion of the filter catheter;

expanding and positioning the tapered dilator tip to extend distally beyond and cover an open distal end of the vascular delivery sheath;

introducing the expanded tapered dilator tip of the embolic filter positioning assembly though an arteriotomy, over a first guidewire received in the guidewire lumen of the elongate dilator, and into the patient's arterial vasculature;

advancing a distal end of the embolic filter positioning assembly to position the embolic filter carried on the distal portion of the filter catheter in the patient's aortic arch;

retracting a distal potion of the vascular delivery sheath from over the embolic filter and expanding the embolic filter within the patient's aortic arch; and contracting the tapered dilator tip and retracting said tip proximally into or through the central lumen of the filter catheter.

2. The method of claim 1, wherein expanding the tapered dilator tip comprises inflating the tapered dilator tip and contracting the tapered dilator tip comprises deflating the tapered dilator tip.

3. The method of claim 1, wherein the tapered dilator tip has a conical geometry with a base and positioning the tapered dilator tip to extend distally beyond and cover an open distal end of the vascular delivery sheath comprises detachably mating the base with the open distal end of the vascular delivery sheath.

4. The method of claim 3, wherein the base of the tapered dilator tip is cylindrical and configured to fit inside the open distal end of the vascular delivery sheath.

5. The method of claim 1, further comprising closing a proximal end of the embolic filter and retracting the filter back into the vascular delivery sheath.

6. The method of claim 5, wherein closing the proximal end of the embolic filter comprises a ratcheting a lasso on the proximal end of the embolic filter.

7. The method of claim 1, wherein the embolic filter self-expands within the patient's aortic arch after the distal portion of the vascular sheath is retracted from over the embolic filter.

8. A method for implanting a prosthetic aortic valve in a patient, said method comprising:

placing an embolic filter in the patient's aortic arch as in claim 1;

advancing the prosthetic aortic valve through the embolic filter; and deploying the prosthetic aortic valve in the patient's aortic annulus while the embolic filter remains in place in the aortic arch.

9. The method of claim 8, wherein advancing the prosthetic aortic valve through the embolic filter comprises:

removing the elongate dilator from the central lumen of the filter catheter leaving the first guidewire in place in the central lumen of the filter catheter;

exchanging the first guidewire for an angiography pigtail catheter;

advancing one or more valve placement guidewires through the embolic filter and over the aortic arch in parallel to the embolic filter positioning assembly; and advancing a valve placement catheter carrying the prosthetic valve over the one or more valve placement guidewires.

10. An embolic filter positioning system comprising:

a vascular delivery sheath having a proximal hemostasis valve, an open distal end, and an open lumen extending from the open distal end to the hemostasis valve;

a filter catheter having a proximal end, a distal end, and a central lumen therethrough;

a self-expanding embolic filter attached to the distal end of the filter catheter;

an elongate dilator having a proximal end, a distal end, and a guidewire lumen therethrough;

a tapered dilator tip attached at the distal end of the elongate dilator;

wherein the elongate dilator is configured to be slidably received in the central lumen of the filter catheter, the filter catheter is configured to be slidably received in the open lumen of the vascular delivery sheath, the tapered dilator tip is positionable distally of the distal end of the vascular delivery sheath, and the self-expanding embolic filter is configured to be radially constrained in a proximal portion of the open lumen of the vascular delivery sheath; and wherein the tapered dilator tip has an expanded configuration where it covers the open distal end of the vascular delivery sheath and facilitates entry though an arteriotomy and a contracted configuration where it can be retracted through the central lumen of the filter catheter.

11. The embolic filter positioning system of claim 10, wherein the tapered dilator tip has a conical geometry with a base configured to detachably mate with the open distal end of the vascular delivery sheath.

12. The embolic filter positioning system of claim 11, wherein the base of the tapered dilator tip is cylindrical and configured to fit inside the open distal end of the vascular delivery sheath.

13. The embolic filter positioning system of claim 10, further comprising a handle attached to the proximal end of the filter catheter.

14. The embolic filter positioning system of claim 13, wherein the handle comprises a mechanism for closing a proximal end of the embolic filter prior to retraction of the filter back into the vascular delivery sheath.

15. The embolic filter positioning system of claim 14, wherein the mechanism for closing a proximal end of the embolic filter comprises a ratcheting retractor coupled to a lasso on the proximal end of the embolic filter.

16. The embolic filter positioning system of claim 10, wherein the embolic filter comprises a cylindrical body configured to self-expand in and conform to the inner wall of the patient's aortic arch.

17. The embolic filter positioning system of claim 16, wherein the embolic filter further comprises a port extending across a central passage of cylindrical body, wherein the port is expandable and configured to seal against the outer surfaces of catheters and guidewires advanced therethrough.

18. The embolic filter positioning system of claims 16, wherein the cylindrical body comprises a porous material comprising a fabric of knitted, woven, or nonwoven fibers, filaments, or wires.

19. The embolic filter positioning system of claim 18, wherein the porous material is made of a resilient metal, polymer material, a malleable material, a plastically deformable material, a shape-memory material, or combinations thereof.

20. The embolic filter positioning system of claim 18, wherein the porous material has a pore size chosen to prevent emboli over a predetermined size from passing through.

* * * * *